(12) United States Patent
Kaplan (10) Patent No.: US 11,826,141 B2
(45) Date of Patent: *Nov. 28, 2023

(54) DEVICE AND METHOD FOR DETECTING IF A BEDRIDDEN PERSON LEAVES HIS OR HER BED OR HAS FALLEN

(71) Applicant: KAPCARE SA, Brussels (BE)

(72) Inventor: Philippe Kaplan, Brussels (BE)

(73) Assignee: KAPCARE SA, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/554,753

(22) Filed: Dec. 17, 2021

(65) Prior Publication Data

US 2022/0104728 A1 Apr. 7, 2022

Related U.S. Application Data

(63) Continuation of application No. 16/651,794, filed as application No. PCT/EP2018/076501 on Sep. 28, 2018.

(30) Foreign Application Priority Data

Sep. 29, 2017 (BE) .................................. 2017/5693

(51) Int. Cl.
*A61B 5/11* (2006.01)
*A61B 5/00* (2006.01)
*G08B 21/22* (2006.01)

(52) U.S. Cl.
CPC ............ *A61B 5/1115* (2013.01); *A61B 5/002* (2013.01); *A61B 5/746* (2013.01); *G08B 21/22* (2013.01)

(58) Field of Classification Search
CPC ................................ A61B 5/002; G08B 21/22
See application file for complete search history.

(56) References Cited

U.S. PATENT DOCUMENTS

| | | | | |
|---|---|---|---|---|
| 2012/0140068 A1* | 6/2012 | Monroe | ................ | H04N 7/183 |
| | | | | 348/143 |
| 2012/0154582 A1* | 6/2012 | Johnson | ................ | G16H 40/20 |
| | | | | 340/521 |
| 2013/0100284 A1* | 4/2013 | Fujii | ....................... | H04N 7/18 |
| | | | | 348/135 |
| 2014/0267625 A1* | 9/2014 | Clark | ....................... | G06T 7/70 |
| | | | | 348/46 |
| 2017/0116484 A1* | 4/2017 | Johnson | ............. | A61M 5/1689 |
| 2017/0215770 A1* | 8/2017 | Tanaka | ................... | G06V 20/52 |

* cited by examiner

*Primary Examiner* — Fabricio R Murillo Garcia
(74) *Attorney, Agent, or Firm* — MCCRACKEN & GILLEN LLC (57) ABSTRACT

The present invention relates to a device and a method for detecting whether a bedridden person is getting out of bed or has fallen out of their bed. The device performs an analysis over time of the distances between the sensors of a detector and the objects that are present in the detection field of the detector. The detection is based on variations in said distances and of the locations thereof within the monitored space.

22 Claims, 3 Drawing Sheets

DEVICE AND METHOD FOR DETECTING IF A BEDRIDDEN PERSON LEAVES HIS OR HER BED OR HAS FALLEN

CROSS-REFERENCE TO RELATED APPLICATIONS

The present application is a continuation of Kaplan, U.S. patent application Ser. No. 16/651,794, entitled "DEVICE AND METHOD FOR DETECTING IF A BEDRIDDEN PERSON LEAVES HIS OR HER BED OR HAS FALLEN" and filed on Mar. 27, 2020, which in turn is a U.S. national phase entry of Kaplan, International Patent Application Serial No. PCT/EP2018/076501, entitled "DEVICE AND METHOD FOR DETECTING IF A BEDRIDDEN PERSON LEABES HIS OR HER BED OR HAS FALLEN" and filed on Sep. 28, 2018, which in turn claims priority to Kaplan, Belgium Patent Application No. BE2017/5693, entitled "DISPOSITIF ET METHODE POUR DETECTER QU'UNE PERSONNE ALITEE QUITTE SON LIT OU A CHUTE" and filed on Sep. 29, 2017. The entire contents of all of these applications are incorporated herein by reference.

FIELD OF INVENTION

The invention relates to the field of devices for monitoring bedridden persons, particularly to devices and methods for determining whether a bedridden person is getting out of bed, either voluntarily or involuntarily such as in the case of a fall from the bed, for example, or if someone has fallen somewhere away from their bed.

PRIOR ART

Detecting the fact that someone has voluntarily gotten or fallen out of bed is a major concern, especially in hospitals and retirement homes. This detection is important, for example, when the person is subject to particular conditions or circumstances such as an illness (in particular dementia, Alzheimer's, etc.), a post-operative situation, or has a history of falls. Such monitoring is particularly sought after in care units such as hospitals, care clinics, or retirement homes in order to prevent any deterioration in the condition of patients, although this monitoring can also be performed in other environments.

The pace within care units prevents qualified personnel from being able to monitor all of the bedridden people in order to detect these events. Thus, various devices have been developed to detect them. For example, pressure-sensing devices can be placed under the mattress of the bed, or even on the floor supports of the bed. When the measured pressure does not correspond to the expected pressure from a bedridden person, an alarm can be triggered. However, these detectors lack finesse, especially when it comes to preventing the patient from getting up. Thus, a patient who tries to get up does not trigger the alert, which can cause complications, for example if the patient falls while trying to get out of bed. This device therefore does not make it possible to anticipate any falling or undesirable getting-up, and it only makes it possible to notice that the bedridden person is no longer in bed. These devices are also dependent on the person's weight and lack reliability for lightweight people, which is often the case for a very elderly person. They also raise the question of maintenance and installation and therefore require handling time on the part of the staff.

Alternative devices have therefore been developed. By way of example, we can cite European patent EP 2335232, which describes a bed exit warning system and a method for predicting the likelihood that a user is going to get out of bed. The system includes one or more sensors capable of measuring a physiological characteristic to produce signals that are indicative of the physiological characteristic, as well as a processor that monitors these signals and determines, based on changes in the signals, whether an alarm should be triggered because the user is likely in the process of getting out of bed. However, the method described and the associated device lacks finesse in signal processing and can generate false alerts.

SUMMARY OF THE INVENTION

It is an object of the invention to provide a device and a method that make it possible to determine with better reliability whether an individual is trying to get out of bed and/or gets out of bed and/or has fallen. The expression "improved reliability" is understood to refer to a device and/or method that produces fewer false positives and/or false negatives than known methods and/or devices. Another object of the invention is to provide a device that is easy to install and use.

The invention is defined by the independent claims. The dependent claims define preferred embodiments of the invention.

The invention provides a device for detecting whether a bedridden person is getting or has gotten out of bed or has fallen after having gotten out of bed, the device comprising a detector having a detection field that is capable of covering at least a portion of the bed and at least a portion of the environment thereof, said detector comprising a plurality of distance sensors, each distance sensor being capable of providing distance measurements over time between said sensor and a corresponding obstacle in said detection field, said device further comprising a processing unit that is connected to the detector and configured to process the distance measurements that are provided by the detector's distance sensors. The processing unit is configured to determine the spatial position of each of said obstacles over time and as a function of the distance measured by the detector for the obstacle in question, and to classify each obstacle based on whether the obstacle is located in a first volume or in a second volume, the first volume being a volume that extends vertically upward and/or downward from the surface of said bed, the second volume being a volume that extends outward from the lateral boundaries of the first volume, and in that the processing unit is configured to determine an event concerning said person if the distance measured for at least one obstacle located in the second volume varies by more than a first predetermined value.

Measuring a variation in distance associated with an obstacle located in the second volume makes it possible to provide the processing unit with information relating to the presence of a movement within the second volume, which is a volume adjoining the bed. This movement is indicative of the fact that the bedridden person is getting out of bed.

The device according to the invention is more reliable than one that utilizes pressure sensors, since it is not concerned with what is happening in the bed. In particular, it is not influenced by the physiological characteristics of the person, such as their weight, for example. It is also easier to install and use since it does not have to be connected to the bed.

The device according to the invention is also more reliable and easier to use than the one described in European patent EP 2335232, because the latter also calls for the measurement of physiological characteristics of the bedridden person, but these characteristics can vary greatly from one person to another.

Preferably, the processing unit is configured to classify each obstacle according to whether the obstacle is located in the first volume or in the second volume or in a third volume, the third volume being a volume that extends outward from the outer lateral boundaries of the second volume, and the processing unit is configured to determine an event concerning said person if the distance measured for at least one obstacle located in the second volume varies by more than a first predetermined value, provided that none of the distances measured for the obstacles located in the third volume have varied by more than a second predetermined value during a first time period preceding the moment when the distance measured for the at least one obstacle located in the second volume has varied by more than the first predetermined value.

This makes it possible to prevent a third person entering the room where the bed is located and moving to the edge of the bed from being interpreted by the device to mean that the bedridden person is getting out of bed.

Preferably, the processing unit is configured to determine an event concerning said person if the distances measured for at least a predetermined number of obstacles located in the second volume each vary by more than a first predetermined value, said predetermined number of obstacles being greater than or equal to two.

This makes it possible to prevent an event from being detected if there is not enough volume in movement. Such a preferred device will therefore detect nothing in the event that only the patient's hand protrudes from the bed, for example.

Preferably, the processing unit is configured to calculate the position of the geometric center of a group of obstacles located in the second volume and whose measured distances each vary by more than the first predetermined value, and to determine that the person has fallen from the bed in which they were bedridden when said geometric center is at a height that is less than a reference height. This makes it possible to detect a fall from a bed more reliably and effectively and to not consider the bedridden person to have fallen if he or she is simply sitting on the edge of their bed. It also makes it possible to detect a person falling after having gotten out of bed normally and taken a few steps in the second volume, for example.

The present invention also relates to a method for detecting whether a bedridden person is getting out of bed, the method comprising the following steps: [0014] a) installing a detector so that a detection field of the detector covers at least a portion of the bed and at least a portion of the environment thereof, said detector comprising a plurality of distance sensors, each distance sensor being capable of providing distance measurements over time between said sensor and a corresponding obstacle in said detection field, and said detector being connected to a processing unit that is configured to process the distance measurements that are provided by the distance sensors of the detector, [0015] b) calibrating the detector and the processing unit to define a space to be monitored in the detection field of the detector, this space to be monitored being divided into at least a first volume and a second volume, the first volume being a volume that extends vertically upward and/or downward from the surface of said bed, the second volume being a volume that extends outward from the lateral boundaries of the first volume, [0016] c) determining, by means of the processing unit, the spatial position of each of said obstacles over time and as a function of the distance measured by the detector for the obstacle in question, [0017] d) classifying, by means of the processing unit, each obstacle according to whether the obstacle is located in a first spatial volume or in a second spatial volume, [0018] e) determining, by means of the processing unit, that an event concerning said person is occurring if the distance measured for at least one obstacle located in the second volume varies by more than a first predetermined value.

BRIEF DESCRIPTION OF THE DRAWINGS

These aspects as well as other aspects of the invention will be clarified in the detailed description of particular embodiments of the invention, reference being made to the drawings of the figures, in which.

The drawings of the figures are neither to scale nor proportioned. In general, similar or identical sensors are denoted by identical references in the figures.

DETAILED DESCRIPTION OF EMBODIMENTS OF THE INVENTION

Figure 1:
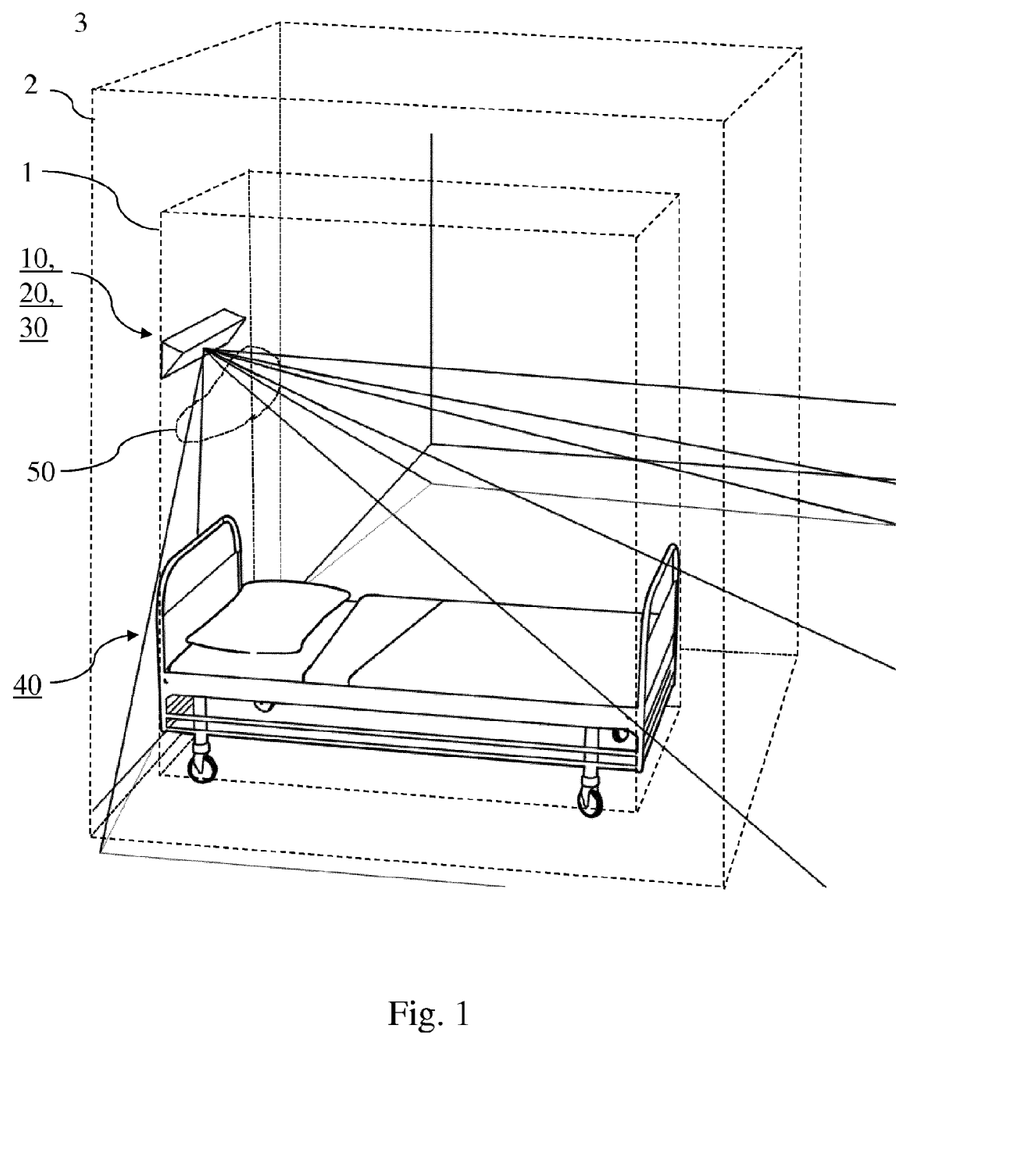
FIG. 1 shows a schematic overview of a device according to the invention.

FIG. 1 shows a schematic overview of a device (10) according to the invention when it is mounted, for example, in a room in which a bed (40) is installed on which a bedridden person (not shown) is to be monitored in order to determine whether he or she is getting out of said bed or has fallen.

The device (10) comprises a detector (20) with a detection field (50) that is capable of covering at least a portion of the bed (40) and at least a portion of the environment thereof. As will readily be understood, the detection field is that portion of the space in which the detector is able to carry out its function. Said detector (20) comprises a plurality of distance sensors, each distance sensor being capable of providing distance measurements over time between said sensor and a corresponding obstacle in said detection field (50). The detector (20) can, for example, be a camera that operates on the time-of-flight (TOF) principle and makes it possible to measure, directly or indirectly and in real time, distances from a three-dimensional scene that is being observed. To do this, a TOF camera illuminates the scene that is in its detection field and calculates the time that the emitted light takes to travel between each photosensitive element (sometimes also called "pixel" in this context) of the camera and a corresponding obstacle in its field of view.

Since the speed of light is constant, this time of flight is directly proportional to the distance between said photosensitive element and the corresponding obstacle. This time-of-flight measurement is carried out independently for each photosensitive element (or "pixel") of the camera. In the example of a TOF camera, it is therefore necessary to understand "a distance sensor that is capable of providing distance measurements over time between said sensor and a corresponding obstacle" as referring to the entirety of a photosensitive element of the camera and to the means available to the camera for calculating the time of flight for said photosensitive element. A concrete example of such a detector is the "SwissRanger 4000" or "SR4000" camera from MESA Imaging, which comprises a matrix of 176×144 photosensitive elements.

The detector (20) is preferably placed or configured to be placed at a height relative to the floor that is greater than the maximum height of the upper surface of said bed, and it is oriented or designed to be oriented such that its detection field (50) covers at least a portion of the bed (40), preferably the entire bed, and at least a portion of the environment thereof.

By way of example, as illustrated in FIG. 1, the detector (20) can be placed against a wall above the headboard (40), although other positions are possible, such as against a wall opposite that against which the bed is placed. The detector (20) can also be arranged so as to have in its detection field (50) at least a portion of the bed, on the one hand, preferably the entirety thereof, and a door that enables entry into and exiting from the room in which the detector (20) is located, on the other hand.

The device (10) further comprises a processing unit (30) that is connected to the detector (20) and configured to acquire and process the distance (or time of flight, which is equivalent to a nearly constant factor) measurements that are supplied by the distance sensors of the detector over time. The processing unit is preferably capable of storing the different measurements that are provided by the distance sensors.

In particular, the processing unit (30) is configured to determine the spatial position of each of said obstacles over time and as a function of the distance measured by the detector for the obstacle in question. The determination of these positions is done by means of a well known geometric calculation, for example in state-of-the-art TOF cameras and applications thereof. Once these positions are known, the processing unit (30) is also configured to classify each obstacle according to whether the obstacle is located in a first spatial volume (1) or in a second spatial volume (2). The first volume (1) is a volume that extends vertically upward and/or downward from the surface of said bed and is therefore typically the volume in which the person is located when in bed. The second volume (2) is a volume that extends outward from the lateral boundaries of the first volume.

The first and second volumes therefore preferably have no common points, apart from possibly their common border. The second volume can have finite or infinite dimensions. The second volume may or may not have external borders.

Figure 2:
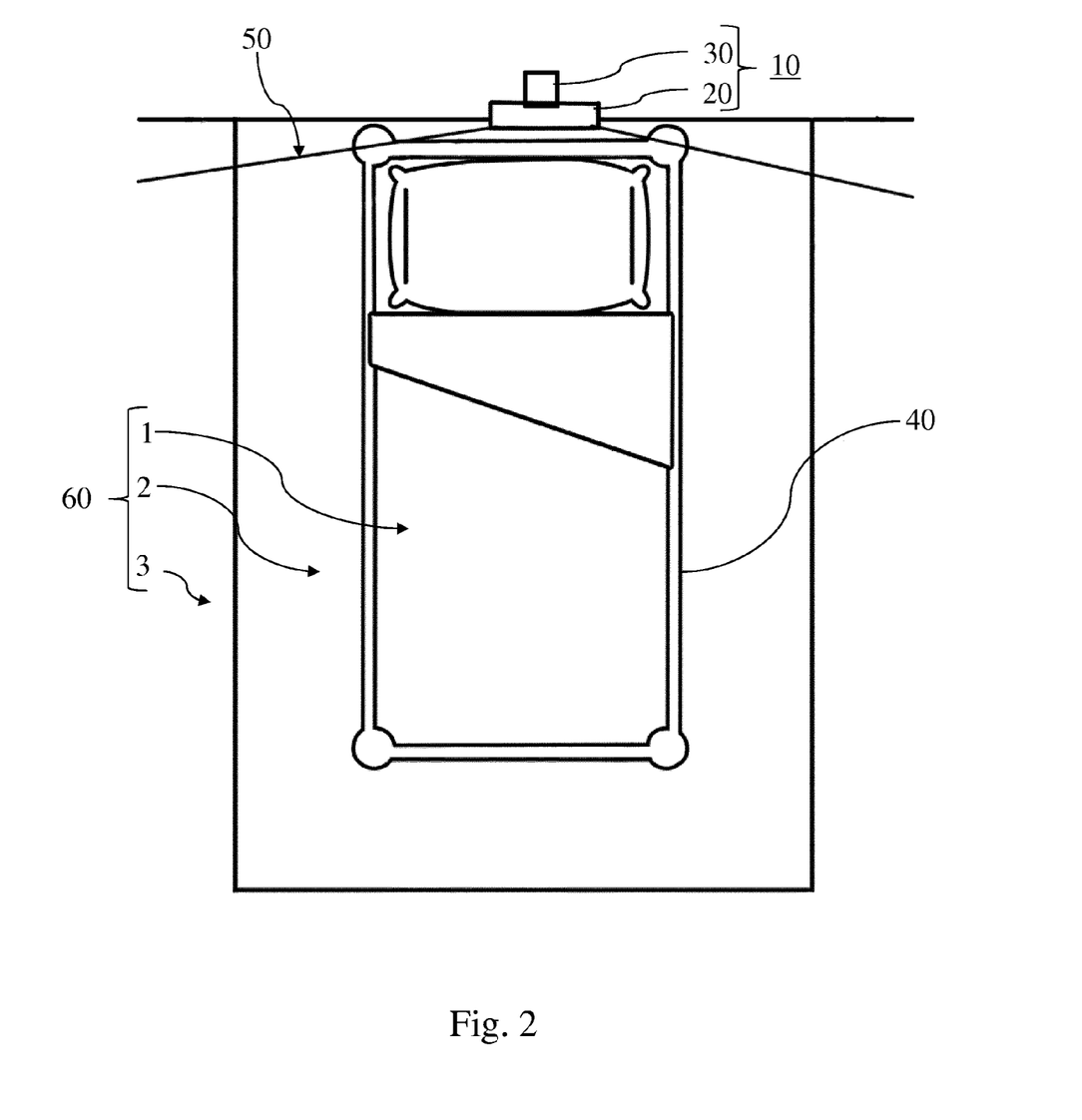
FIG. 2 shows a top view of the device of FIG. 1 according to one embodiment.

FIG. 1 shows an example of first volume (1) and second volume (2) in dotted lines. Although this is not clearly visible in the figure, it should be understood that these two volumes are preferably exclusive, meaning that they have no common points apart from possibly their common border, which is the outer envelope of the first volume (1) in the case of FIG. 1. FIG. 2 shows a top view of the device of FIG. 1 according to one embodiment that enables the orthogonal projections of the first volume and the second volume on the floor to be seen. In this example, the distance sensors that point toward the bed pillow, for example, will each provide the distance between the sensor and a corresponding zone on the pillow in its line of sight when the bed is not occupied. The values of these distances will enable the processing unit (30) to determine that the corresponding points of the pillow are in the first volume (1), while the distance sensors that point toward the parts of the floor that are close to the footprint of the bed, for example, will each provide the distance between the sensor and a corresponding zone on the floor in its line of sight. The value of these distances which will enable the processing unit to determine that the corresponding points on the floor are in the second volume (2).

The processing unit (30) is also configured to determine an event concerning said person if the distance measured for at least one obstacle located in the second volume varies by more than a first predetermined value (a first threshold). In other words, the processing unit will determine that an event concerning the person is occurring if the processing unit detects that a significant movement is taking place in the second volume (2). The event may be the fact that the person is getting out of bed or attempting to do so, or has fallen out of bed, or has fallen somewhere away from their bed.

The processing unit (30) can evaluate said variation in distance periodically or continuously, in the latter case within the limits of the maximum rate at which the detector can provide the distance information. In the case of a periodic evaluation, the processing unit can evaluate said variation in distance every 5 seconds, every 4 seconds, every 3 seconds, every 2 seconds, every second, or every 0.5 second, for example. Alternatively, an initial state that is recorded at time t0 can serve as a point of comparison for the variations in distance measured at each time t following to. The time between time t0 and the next time t can then be greater than 1 minute, or 5 minutes, or 10 minutes. It will readily be understood that the initial state at to can be reset regularly, for example every 10 minutes, or every 30 minutes, or even every hour.

The processing unit (30) can be any means that makes it possible to receive and analyze the distance measurements that are provided by the detector (20), particularly as a function of time. It can be a microprocessor, for example, that comprises a program for analyzing the data corresponding to the distance measurements that are supplied by the detector.

Note that the processing unit (30) can be grouped with the detector (20), for example within the same housing. Alternatively, the detector (20) can be separated from the processing unit (30) and provided with—preferably wireless—data communication means such as WI-FI (standard IEEE 802.11), for example, thereby enabling data to be transferred to the processing unit (30). The processing unit (30) then comprises means for receiving the data that are transmitted by the detector (20) via the communication means. In this case, said data include at least the distance measurements or the times of flight provided by the distance sensors of the detector (20).

Preferably, the processing unit (30) is configured to classify each obstacle according to whether the obstacle is located in the first volume (1) or in the second volume (2) or in a third volume (3). In this case, the third volume is a volume that extends outward from the outer lateral boundaries of the second volume—which implies, in this preferred case, that the second volume has finite and well defined outer boundaries. In the example illustrated in FIG. 1, the third volume (3) is the volume of the space that surrounds the second volume (2) without containing it. The second and third volumes therefore preferably have no common points, apart from possibly their common border.

Figure 3:
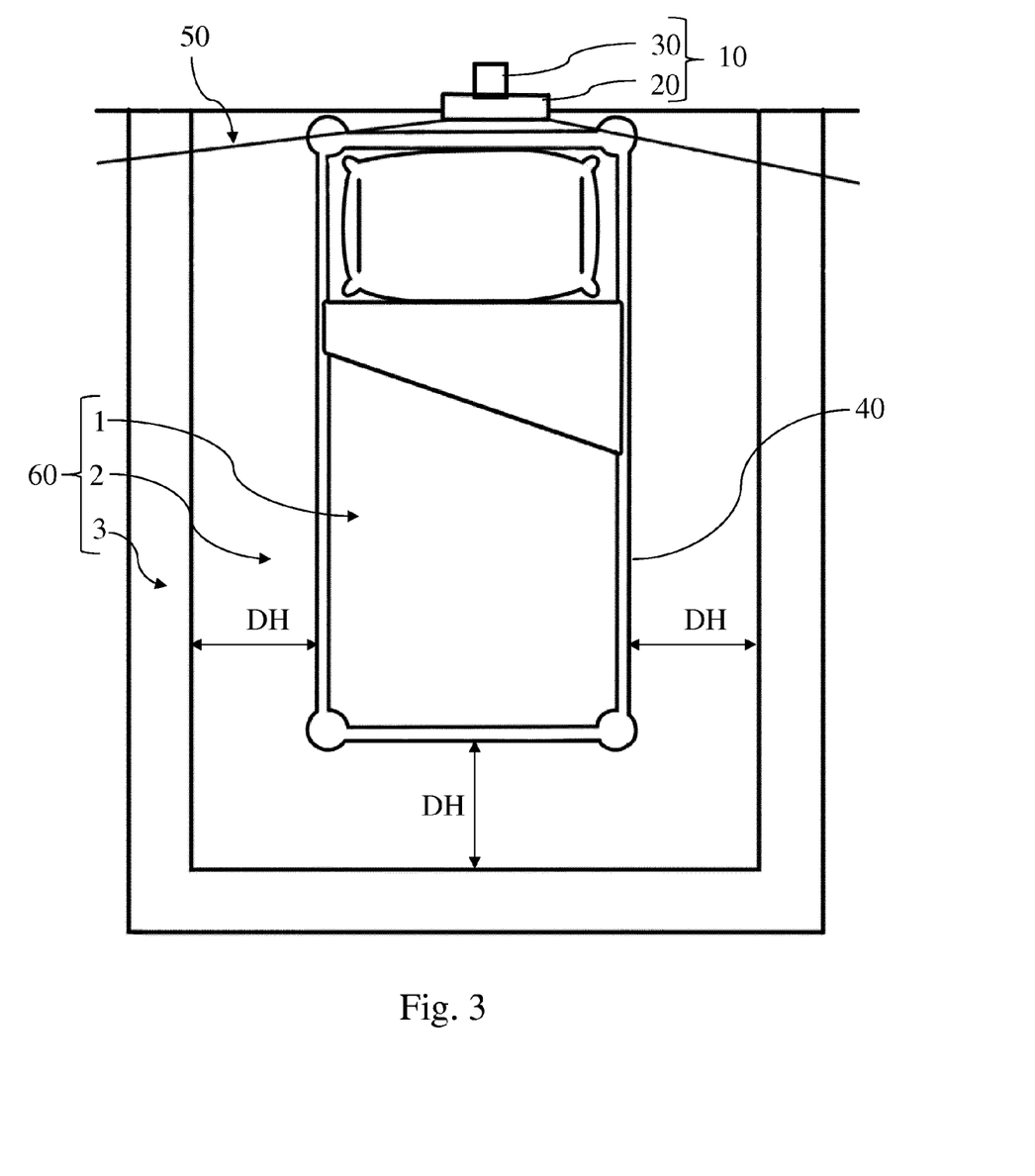
FIG. 3 shows a top view of the device of FIG. 1 according to a preferred embodiment of the invention.

FIG. 3 shows a top view of the device of FIG. 1 according to this preferred embodiment of the invention that enables the orthogonal projections of the first volume (1), the second volume (2), and the third volume (3) on the floor to be seen. In the case of FIG. 3, the third volume has external borders. It should be noted that the third volume may have no external borders and extend to infinity (case not illustrated). In this preferred version, the processing unit (30) is configured to determine an event concerning said person if the distance that is measured for at least one obstacle located in the second volume (2) varies by more than a first predetermined value, provided that none of the distances measured for the obstacles located in the third volume (3) have varied by more than a second predetermined value during a first time period preceding the moment when the distance measured for the at least one obstacle located in the second volume (2) has varied by more than the first predetermined value.

In other words, the processing unit will determine that an event concerning the person is occurring if the processing unit detects that a significant movement has taken place in the second volume without this movement having been preceded during the first time period of another significant movement in the third volume. The event in question may be the fact that the person is getting out of bed or attempting to do so or has fallen out of bed. On the other hand, the processing unit will not determine that an event concerning the person is occurring if a movement is first detected in the third volume (3) and if the detection of this movement is followed in the first time period by detection of movement in the second volume (2). Thus, the device will detect nothing if it is the movement of a person approaching the bed, which is the aim that is being pursued in this preferred version.

The first time period is a period of 5 seconds, preferably 4 seconds, preferably 3 seconds, preferably 2 seconds, preferably 1 second, and preferably 0.5 seconds, for example.

In each of the preceding cases, the processing unit (30) is preferably configured to determine an event concerning said person if the distances measured for at least a predetermined number of obstacles located in the second volume (2) each vary more than a first predetermined value, said predetermined number of obstacles being greater than or equal to two. The event in question may be the fact that the person is getting out of bed or attempting to do so or has fallen out of bed. According to this preferred version, the device is prevented from detecting an event if only a small material volume moves in the second volume, such as for example if the bedridden person only hangs his or her arm outside of the first volume (1). This prevents false alerts.

Preferably, the first volume (1), the second volume (2) and the third volume (3) are each formed by one or more parallelepipeds, preferably rectangular parallelepipeds as illustrated in FIG. 1, for example.

Preferably, the first volume (1) is delimited laterally by surfaces perpendicular to the upper surface of the bed and tangent to the edges of the bed (40), and by a horizontal upper surface that is disposed no more than 100 cm from the upper surface of the bed or 80 cm from the top surface of the bed or even 50 cm from the top surface of the bed. The upper surface of the bed is, for example, the upper surface of the mattress of the bed when the mattress is horizontal and the bed is in the highest position vertically. Alternatively, the first volume (1), the second volume (2) and the third volume (3) can be formed of concentric spheres that are centered on the detector.

In the case of rectangular parallelepipeds, the second volume (2) is preferably formed by a set of spatial points, each of which is located at a horizontal distance DH (see FIG. 3) between zero and two meters from the lateral boundaries of the first volume (1). More preferably, the second volume is formed by a set of spatial points, each of which is located at a horizontal distance DH (see FIG. 3) between zero and one meter from the lateral boundaries of the first volume. Even more preferably, the second volume is formed by a set of spatial points, each of which is located at a horizontal distance DH (see FIG. 3) between zero and one 50 cm from the lateral boundaries of the first volume. Preferably, the second volume is a volume that extends from the floor to at least one installation height of the detector (20).

In each of the preceding cases, or alternatively, the processing unit (30) is preferably configured to calculate the position of the geometric center of a group of obstacles located in the second volume (2) and whose measured distances each vary by more than the first predetermined value, and to determine that the person has fallen when said geometric center is at a height that is less than a reference height. Such a preferred version thus makes it possible to detect that the person has had a fall. It should be noted that the geometric center of the group of obstacles, which is the average spatial position of the points of the group of obstacles should not be confused here with the center of gravity or center of mass thereof.

Preferably, the reference height and the height of the upper surface of the bed relative to the floor on which it rests. For example, it is the height of the upper surface of the mattress from the bed.

Preferably, the processing unit (30) comprises a memory in which the first predetermined value is stored and/or in which the second predetermined value is stored and/or in which the reference height is stored.

The first predetermined value can be stored in this memory during the manufacture of the device (10), or it can be recorded following empirical measurements during the installation of the device by carrying out tests with the bedridden person. In the latter case, the first determined value is selected during the application of the device within a person's room and stored in the memory at that time. This value is considered to mean, for example, that a variation in distance corresponding to a non-negligible movement has been detected by the device in the second volume (2). The same applies to the second predetermined value.

The first predetermined value can contain a plurality of values corresponding to a plurality of morphologies in order to adapt the device to people of variable sizes. The first predetermined value can correspond to a minimum variation in distance—for example a variation in distance of greater than 5 cm, or even greater than 10 cm, or even greater than 15 cm, and preferably greater than 20 cm. Alternatively or in addition, the higher predetermined value may correspond to a minimum number of sensors for which a variation in distance has been measured. This value can also correspond to a minimum percentage or a minimum proportion of distance sensors associated with a particular volume for which a variation in distance has been measured, such as for example more than 5% of the distance sensors, or preferably more than 10% of the distance sensors, or more preferably more than 20% of the distance sensors. In addition, the higher predetermined value can correspond to the measurement of a variation in distance for a minimum number or percentage of distance sensors having a variation in distance that is greater than a minimum distance. Thus, and by way of example, a higher predetermined value may correspond to at least 1 distance sensor, or to at least 5 distance sensors, or to at least 10 distance sensors, or to 10% of distance sensors associated with a volume whose variation in distance is greater than 5 cm, or 10 cm. Other combinations are possible. The first predetermined value may include a plurality of values, each associated with a threshold value that is associated with each volume (1, 2). In point of fact, the movements can have different amplitudes in the different volumes and have a plurality of threshold values, each corresponding to a particular volume, which enables finer processing of the information. The same applies to the second predetermined value.

Preferably, the device (10) comprises visual and/or audio means, and the processing unit (30) is configured to activate said visual and/or audio means when said event concerning said person is detected.

This enables a third party to notice that said event concerning the person has been detected. These visual and/or audio means are preferably placed at a distance from the detector (10), for example in a different room from where the monitored bed (40) is located, such as a monitoring station in a care center, for example. Alternatively, the device (10) can include means for transmitting an alert signal to a third-party object when an event concerning the person is detected, in which case the third-party object can then activate visual and/or audio means when it receives such an alert signal and/or transmit this alert signal to yet another third-party object. The third-party object can be a smartphone on which an application is running, for example, rendering the smartphone capable of receiving said alert signal and sounding an audible alarm and/or displaying information indicating the occurrence of the event in question. Alternatively, the alert signal can be a transient signal stored in memory that does not trigger any alarm but is capable of triggering an alarm if certain additional conditions are met.

In a preferred version of the device (10), the processing unit (30) is configured to store the alert signal in a memory and to trigger an alarm or send an alert signal as a function of the analysis of the subsequent alert signals. Thus, when the processing unit has issued an alert signal following the analysis of the variations in distance within the three volumes (1, 2, 3), the processing unit is configured to suppress this alert signal if no subsequent variation in distance is measured successively within the third volume, within the second volume, and finally within the first volume. The processing unit (30) is preferably configured to limit this possibility of suppressing the alert signal for a limited period of time. Thus, after a time period of greater than 1 minute, or even greater than 2 minutes, even greater than 3 minutes, even greater than 4 minutes, or even greater than 5 minutes, if no variation in distance is successively measured from the third volume at the first volume, the processing unit (30) is configured to emit the alert signal in order to activate any visual or audio means as described above. [0047] According to this preferred device, no alarm is generated when movements are detected from outside the monitored space up to the bed, indicating either that the person who was previously in bed has returned there, or that a third person has intervened and accompanied the patient to bed, thus reducing the triggering of an unwanted alert.

The present invention also relates to a method for detecting whether a bedridden person is getting out of bed (40), the method comprising the following steps: [0049] a) installing a detector (20) so that a detection field (50) of the detector covers at least a portion of the bed (40) and at least a portion of the environment thereof, said detector (20) comprising a plurality of distance sensors, each distance sensor being capable of providing distance measurements over time between said sensor and a corresponding obstacle in said detection field (50), and said detector (20) being connected to a processing unit (30) that is configured to process the distance measurements that are provided by the distance sensors of the detector, [0050] b) calibrating the detector and the processing unit to define a space to be monitored in the detection field of the detector, this space to be monitored being divided into at least a first volume (1) and a second volume (2), the first volume being a volume that extends vertically upward and/or downward from the surface of said bed, the second volume being a volume that extends outward from the lateral boundaries of the first volume, [0051] c) determining, by means of the processing unit (30), the spatial position of each of said obstacles over time and as a function of the distance measured by the detector for the obstacle in question, [0052] d) classifying, by means of the processing unit (30), each obstacle according to whether the obstacle is located in the first volume or in the second volume, [0053] e) determining, by means of the processing unit (30), that an event concerning said person is occurring if the distance measured for at least one obstacle located in the second volume varies by more than a first predetermined value.

The present invention has been described in relation to specific embodiments, which have been provided purely for illustration and should not be regarded as limiting. In general, it will be obvious to those skilled in the art that the present invention is not limited to the examples that have been illustrated and/or described above. The presence of reference numerals in the drawings cannot be regarded as limiting, including when these numerals are indicated in the claims.

The use of the verbs "to comprise," "to include," "to contain," or any other variant, as well as conjugations thereof, cannot in any way exclude the presence of sensors other than those mentioned. The use of the indefinite article "a" or "an," or of the definite article "the," to introduce a sensor does not exclude the presence of a plurality of these sensors.

The invention can also be described as follows: a device (10) and a method for detecting whether a bedridden person is getting out of bed or attempting to do so or has fallen. The device performs an analysis over time of the distances between the sensors of a detector (20) and the objects that are present in the detection field (50) of the detector. The detection is based on variations in said distances and of the locations thereof within the monitored space (60).

I claim:

1. A device for detecting whether a bedridden person is getting or has gotten out of a bed or has fallen after having gotten out of the bed, the device comprising a detector having a detection field that is capable of covering at least a portion of the bed and at least a portion of an environment of the bed, said detector comprising a plurality of distance sensors, each distance sensor of said plurality of distance sensors being capable of providing distance measurements over time between each said distance sensor of said plurality of distance sensors and a corresponding obstacle in a line of sight of the distance sensor, said device further comprising a processing unit that is connected to the detector and configured to process the distance measurements that are provided by each distance sensor of said plurality of distance sensors of the detector, wherein the processing unit is configured to determine respective three-dimensional spatial positions of each of said corresponding obstacles over time and as a function of said distance measurements, and to classify over time each of said corresponding obstacles according to whether a corresponding obstacle is located in a first volume or in a second volume, the first volume being a volume that extends vertically upward and/or downward from a surface of said bed and is delimited laterally by surfaces perpendicular to an upper surface of the bed when in horizontal position and tangent to the edges of the bed and by a horizontal plane at a distance from a top surface of the bed, and the second volume being a volume that extends outward from outer lateral boundaries of the first volume and surrounds the first volume, and wherein the first volume and the second volume are mutually exclusive, and wherein the processing unit is configured to determine that the bedridden person is getting or has gotten out of the bed or has fallen after having gotten out of the bed when the distance measurement for at least one obstacle of said corresponding obstacles which is classified as being located in the second volume has varied by more than a first predetermined value.

2. The device as set forth in claim 1, wherein the processing unit is configured to classify over time each of said corresponding obstacles according to whether a corresponding obstacle is located in the first volume or in the second volume or in a third volume, the third volume being a volume that extends outward from outer lateral boundaries of the second volume, and in that the processing unit is configured to determine an event concerning said person if the distance measurement for the at least one obstacle of said corresponding obstacles that has been classified as being located in the second volume has varied by more than the first predetermined value, provided that none of the distance measurements for each obstacle of said corresponding obstacles that have been classified as being located in the third volume have varied by more than a second predetermined value during a first time period preceding a moment when the distance measured for the at least one obstacle of said corresponding obstacles that has been classified as being located in the second volume has varied by more than the first predetermined value.

3. The device as set forth in claim 1, wherein the processing unit is configured to determine an event concerning said person if distance measurements for at least a predetermined number of obstacles of said corresponding obstacles that have been classified as being located in the second volume each have varied by more than the first predetermined value, said at least a predetermined number of obstacles being greater than or equal to two.

4. The device as set forth in claim 1, wherein the first volume and the second volume are each formed by one or more parallelepipeds, preferably rectangular parallelepipeds, each parallelepipeds having planar boundaries on all sides.

5. The device as set forth in claim 4, wherein the second volume is formed by a set of spatial points, each spatial point of said spatial points being located at a horizontal distance between zero and two meters from the outer lateral boundaries of the first volume.

6. The device as set forth in claim 5, wherein the second volume is formed by a set of spatial points, each of said spatial points being located at a horizontal distance between zero and one meter from the outer lateral boundaries of the first volume.

7. The device as set forth in claim 1, wherein the detector is placed or configured to be placed at a height greater than a maximum height of an upper surface of said bed.

8. The device as set forth in claim 1, wherein the second volume is a volume that extends from a floor to at least an installation height of the detector.

9. The device as set forth in claim 1, wherein the processing unit is configured to calculate a spatial position of a geometric center of a group of obstacles of said corresponding obstacles, the distance measurements of which have each varied by more than the first predetermined value and that have been classified as being located in the second volume, and to determine that the bedridden person has fallen from the bed when said geometric center is located at a height that is less than a reference height.

10. The device as set forth in claim 9, wherein the reference height is a height of an upper surface of the bed relative to a floor on which the bed rests.

11. The device as set forth in claim 1, wherein the processing unit comprises a memory in which the first predetermined value is stored.

12. The device as set forth in claim 1, wherein the device comprises visual and/or audio means and in that the processing unit is configured to activate said visual and/or audio means when said event concerning said person is detected.

13. A device for detecting whether a bedridden person is getting or has gotten out of a bed or has fallen after having gotten out of the bed, the device comprising a detector having a detection field that is capable of covering at least a portion of the bed and at least a portion of an environment of the bed, said detector comprising a plurality of distance sensors, each distance sensor of said plurality of distance sensors being capable of providing distance measurements over time between each said distance sensor of said plurality of distance sensors and a corresponding obstacle in a line of sight of the distance sensor, said device further comprising a processing unit that is connected to the detector and configured to process the distance measurements that are provided by each distance sensor of said plurality of distance sensors of the detector, wherein the processing unit is configured to determine respective three-dimensional spatial positions of each of said corresponding obstacles over time and as a function of said distance measurements, and to classify over time each of said corresponding obstacles according to whether each of the said corresponding obstacles is located in a first volume or in a second volume, the first volume being a volume that extends vertically upward and/or downward from a surface of said bed and is delimited laterally by surfaces perpendicular to an upper surface of the bed when in horizontal position and tangent to the edges of the bed and by a horizontal plane at a distance from a top surface of the bed, and the second volume being a volume that extends outward from outer lateral boundaries of the first volume and surrounds the first volume, and wherein the first volume and the second volume are mutually exclusive, and wherein the processing unit is configured to ignore those of said corresponding obstacles that have been classified as being located in the first volume and to consider only those of said corresponding obstacles that have been classified as being located in the second volume, and to determine that the bedridden person is getting or has gotten out of the bed or has fallen after having gotten out of the bed when at least one obstacle of said corresponding obstacles has been classified as being located in the second volume and the distance measurement for said at least one obstacle of said corresponding obstacles classified as being located in the second volume has varied by more than a first predetermined value.

14. The device as set forth in claim 13, wherein the processing unit is configured to classify each said corresponding obstacle according to whether the said corresponding obstacle is located in the first volume or in the second volume or in a third volume, the third volume being a volume that extends outward from outer lateral boundaries of the second volume, and in that the processing unit is configured to determine an event concerning said person if the distance measurement for at least one obstacle of said corresponding obstacles that has been classified as being located in the second volume has varied by more than the first predetermined value, provided that none of the distance measurements for each obstacle of said corresponding obstacles that have been classified as being located in the third volume have varied by more than a second predetermined value during a first time period preceding a moment when the distance measured for the at least one obstacle of said corresponding obstacles that have been classified as being located in the second volume has varied by more than the first predetermined value.

15. The device as set forth in claim 13, wherein the processing unit is configured to determine an event concerning said person if distance measurements for at least a predetermined number of obstacles of said corresponding obstacles that have been classified as being located in the second volume each vary by more than the first predetermined value, said at least a predetermined number of obstacles being greater than or equal to two.

16. The device as set forth in claim 13, wherein the first volume and the second volume are each formed by one or more parallelepipeds, preferably rectangular parallelepipeds, each parallelepipeds having planar boundaries on all sides.

17. The device as set forth in claim 16, wherein the second volume is formed by a set of spatial points, each spatial point of said set of spatial points being located at a horizontal distance between zero and two meters from the outer lateral boundaries of the first volume.

18. The device as set forth in claim 17, wherein the second volume is formed by a set of spatial points, each spatial point of said spatial points being located at a horizontal distance between zero and one meter from the outer lateral boundaries of the first volume.

19. The device as set forth in claim 13, wherein the detector is placed or configured to be placed at a height greater than a maximum height of the upper surface of said bed.

20. The device as set forth in claim 13, wherein the second volume is a volume that extends from a floor to at least an installation height of the detector.

21. The device as set forth in claim 13, wherein the processing unit is configured to calculate a spatial position of a geometric center of a group of obstacles of said corresponding obstacles, the distance measurements of which have each varied by more than the first predetermined value and that have been classified as being located in the second volume, and to determine that the bedridden person has fallen from the bed when said geometric center is located at a height that is less than a reference height.

22. A method for detecting whether a bedridden person is getting or has gotten out of a bed or has fallen after having gotten out of the bed, the method comprising steps of:

a) installing a detector so that a detection field of the detector covers at least a portion of the bed and at least a portion of an environment of the bed, said detector comprising a plurality of distance sensors, each distance sensor of said plurality of distance sensors being capable of providing distance measurements over time between each said distance sensor of said plurality of distance sensors and a corresponding obstacle in a line of sight of the distance sensor, and said detector being connected to a processing unit that is configured to process the distance measurements that are provided by the each distance sensor of said plurality of distance sensors of the detector, b) calibrating the detector and the processing unit to define a space to be monitored in the detection field of the detector, the space to be monitored being divided into at least a first volume and a second volume, the first volume being a volume that extends vertically upward and/or downward from a surface of said bed and is delimited laterally by surfaces perpendicular to an upper surface of the bed when in horizontal position and tangent to the edges of the bed and by a horizontal plane at a distance from a top surface of the bed, the second volume being a volume that extends outward from outer lateral boundaries of the first volume and surrounds the first volume, and wherein the first volume and the second volume are mutually exclusive, c) determining, by means of the processing unit, respective three-dimensional spatial positions of each of said corresponding obstacles over time and as a function of said distance measurements, d) classifying, by means of the processing unit, each of said corresponding obstacles over time according to whether each of the said corresponding obstacles is located in the first volume or in the second volume, e) determining, by means of the processing unit, that an event concerning said person is occurring if the distance measurement for at least one obstacle of said corresponding obstacles that has been classified as being located in the second volume has varied by more than a first predetermined value.

* * * * *